United States Patent
Champion et al.

(10) Patent No.: US 10,588,917 B2
(45) Date of Patent: Mar. 17, 2020

(54) MIXTURES OF HUMAN MILK OLIGOSACCHARIDES COMPRISING 3'-O-SIALYLLACTOSE

(71) Applicant: Glycom A/S, Hørsholm (DK)

(72) Inventors: Elise Champion, Toulouse (FR); Bruce McConnell, La Tour de Peilz (CH); Gyula Dekany, Sinnamon Park (AU)

(73) Assignee: GLYCOM A/S, Hørsholm (DK)

(*) Notice: Subject to any disclaimer, the term of this patent is extended or adjusted under 35 U.S.C. 154(b) by 20 days.

(21) Appl. No.: 15/561,684

(22) PCT Filed: Mar. 31, 2016

(86) PCT No.: PCT/IB2016/051823
§ 371 (c)(1),
(2) Date: Sep. 26, 2017

(87) PCT Pub. No.: WO2016/157108
PCT Pub. Date: Oct. 6, 2016

(65) Prior Publication Data
US 2018/0078574 A1    Mar. 22, 2018

(30) Foreign Application Priority Data
Mar. 31, 2015   (EP) .................................... 15162014
Mar. 31, 2015   (EP) .................................... 15162024

(51) Int. Cl.
| | |
|---|---|
| *A61K 31/702* | (2006.01) |
| *C12P 19/14* | (2006.01) |
| *C07H 3/06* | (2006.01) |
| *C12P 19/00* | (2006.01) |
| *C07H 5/06* | (2006.01) |
| *C12P 19/18* | (2006.01) |
| *C12P 19/26* | (2006.01) |
| *C07H 1/00* | (2006.01) |
| *A61K 31/7016* | (2006.01) |

(52) U.S. Cl.
CPC ........ *A61K 31/702* (2013.01); *A61K 31/7016* (2013.01); *C07H 1/00* (2013.01); *C07H 3/06* (2013.01); *C07H 5/06* (2013.01); *C12P 19/00* (2013.01); *C12P 19/14* (2013.01); *C12P 19/18* (2013.01); *C12P 19/26* (2013.01); *C12Y 302/01018* (2013.01)

(58) Field of Classification Search
None
See application file for complete search history.

(56) References Cited

U.S. PATENT DOCUMENTS

| | | |
|---|---|---|
| 2002/0025560 A1 | 2/2002 | Koizumi et al. |
| 2003/0129278 A1 | 7/2003 | Stahl et al. |

FOREIGN PATENT DOCUMENTS

| | | |
|---|---|---|
| EP | 2522232 A1 | 11/2012 |
| WO | 0104341 | 1/2001 |
| WO | 2007101862 | 9/2007 |
| WO | 200959996 | 5/2009 |
| WO | 2010100979 | 9/2010 |
| WO | 2010115934 | 10/2010 |
| WO | 2010115935 | 10/2010 |
| WO | 2011100980 | 8/2011 |
| WO | 2012069416 | 5/2012 |
| WO | 2012092153 | 7/2012 |
| WO | 2012155916 | 11/2012 |
| WO | 2012156897 | 11/2012 |
| WO | 2012156898 | 11/2012 |
| WO | 2013044928 | 4/2013 |
| WO | 2013091660 | 6/2013 |
| WO | 2013139344 | 9/2013 |
| WO | 2013148134 | 10/2013 |
| WO | 2014187464 A1 | 11/2014 |
| WO | 2015036138 | 3/2015 |

OTHER PUBLICATIONS

Klindworth, A., et al. "Evaluation of general 16S ribosomal RNA gene PCR primers for classical and next-generation sequencing-based diversity studies," Nucleic Acids Research, 2013, vol. 41(1), pp. 1-11.
Urashima, T. et al. (2011) Nutrition and Diet Research Progress: Milk Oligosaccharides. New York: Nova Science Publishers, Inc.

*Primary Examiner* — Eric Olson
(74) *Attorney, Agent, or Firm* — Neal, Gerber & Eisenberg LLP

(57) ABSTRACT

A mixture of human milk oligosaccharides that consists essentially of 3'-O-sialyllactose, a component A which is either 3-O-fucosyllactose or lacto-N-tetraose, a component B which is 3-O-fucosyl-3'-O-sialyllactose when component A is 3-O-fucosyllactose and sialyllacto-N-tetraose a, when component A is lacto-N-tetraose and optionally lactose as a fourth component. The mixtures are made by treating 3'-O-sialyllactose and component A with an α2,3-transsialidase. The mixtures are for use in anti-bacterial and anti-viral compositions, and for promoting the development of *Bifidobacterium* and *Barnesiella*.

5 Claims, No Drawings

MIXTURES OF HUMAN MILK OLIGOSACCHARIDES COMPRISING 3'-O-SIALYLLACTOSE

CROSS-REFERENCE TO RELATED APPLICATIONS

This application is a national stage entry pursuant to 35 U.S.C. 371 of International Patent Application No. PCT/IB2016/051823, filed on Mar. 31, 2016, which claims priority to European Patent Application No. 15162014.3, filed Mar. 31, 2015, and European Patent Application No. 15162024.2, filed Mar. 31, 2015, the contents of all of which are fully incorporated herein by reference.

FIELD OF THE INVENTION

The present invention relates to ternary mixtures of Human Milk Oligosaccharides ("HMOs"), particularly mixtures of 3'-O-sialyllactose (3'-SL), a component A which is 3-O-fucosyllactose (3-FL) or lacto-N-tetraose (LNT), and a component B which 3-O-fucosyl-3'-O-sialyllactose (FSL) when component A is 3-FL or sialyllacto-N-tetraose a (LST-a) when component A is LNT, a process for making the ternary mixtures, and applications of the ternary mixtures in human health.

BACKGROUND OF THE INVENTION

HMOs have become the subject of much interest in recent years due to their roles in numerous biological processes occurring in the human organism. Mammalian milk contains at least 130 of these complex oligosaccharides (Urashima et al: *Milk Oligosaccharides*, Nova Biomedical Books, New York, 2011, ISBN: 978-1-61122-831-1).

Previously, the only source of HMOs had been mammalian milk which contains mostly water, together with 55-70 g/l lactose, 24-59 g/l lipids, ca. 13 g/l proteins, 5-15 g/l HMOs and ca. 1.5 g/l minerals.

However, efforts to develop processes for synthesizing these oligosaccharides have increased significantly in the last ten years due to their roles in numerous human biological processes. In this regard, processes have been developed for producing HMOs by microbial fermentations, enzymatic processes, chemical syntheses, or combinations of these technologies. For example, by chemical processes, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, and 6'-SL and salts thereof can be made as described in WO 2010/100979. As examples of biotechnological processes, WO 01/04341 and WO 2007/101862 describe how to make core human milk oligosaccharides optionally substituted by fucose or sialic acid using genetically modified *E. coli*. As an example of enzymatic processes, sialylated oligosaccharides can be made as described in EP-A-577580.

Efforts have also been made to develop processes for synthesizing enzymatically mixtures of HMO oligosaccharides, without having to synthesize all of the component oligosaccharides of the mixture as described in WO 2012/156897 and WO 2012/156898. Such processes have provided reaction mixtures containing a plurality of different oligosaccharides.

However, better processes have been sought for the synthesis of mixtures of HMOs, especially mixtures consisting of three HMOs, particularly 3'-SL, 3-FL and FSL, or 3'-SL, LNT and LST-a.

Evidence is accumulating that the resident community of microbes, called the microbiome, in the human digestive tract plays a major role in health and disease. When the normal composition of the microbiome is thrown off balance, the human host can suffer consequences. Recent research has implicated microbiome imbalances in disorders as diverse as cancer, obesity, inflammatory bowel disease, psoriasis, asthma, and possibly even autism. HMOs are believed to positively modulate the microbiome, and they are of increasing interest for this purpose. However, the remarkable diversity of HMOs, coupled with their lack of availability, has hampered studies of the specific functions of individual HMOs. There is a clear need for specific HMOs or combinations of HMOs to modulate the microbiome in a desired manner, so as to address specific human health issues.

SUMMARY OF THE INVENTION

One aspect of this invention relates to a first mixture of HMOs consisting essentially of 3'-O-sialyllactose (3'-SL), a component A which is 3-O-fucosyllactose (3-FL) or lacto-N-tetraose (LNT), and a component B which is either 3-O-fucosyl-3'-O-sialyllactose (FSL) when component A is 3-FL, or sialyllacto-N-tetraose a (LST-a) when component A is LNT.

Another aspect of this invention relates to a process for making the first HMO mixture by reacting a 3'-SL donor and a component A acceptor in the presence of an α2,3-transsialidase and then removing lactose and the α2,3-transsialidase from the reaction medium.

Another aspect of this invention relates to a second mixture of HMOs which consists essentially of 3'-SL, a component A which is 3-FL or LNT, a component B which is either FSL when component A is 3-FL, or LST-a when component A is LNT, and lactose.

Another aspect of this invention relates to a process for making the second HMO mixture by reacting a 3'-SL donor and a component C acceptor in the presence of an α2,3-transsialidase, and then removing the α2,3-transsialidase from the reaction medium. The resulting mixture is the second HMO mixture of this invention.

One aspect of this invention relates to anti-infective compositions for treating viral and/or bacterial infections, wherein said compositions comprise either 3'-SL, 3-FL and FSL, or 3'-SL, LNT and LST-a. These compositions contain mixtures of a plurality of different HMOs with novel properties and biological activities. Specifically, the compositions increase *Bifidobacterium* abundance and *Barnesiella* abundance of the microbiome in a human. Further, the compositions inhibit pathogen binding to the host and thereby protect the host from infection. The compositions can also be used to treat and/or reduce the risk of a broad range of viral and/or bacterial infections of a human. The anti-infective composition is advantageously the first or second mixture of this invention, more advantageously the first mixture, as described above.

Another aspect of this invention relates to a method of modulating the microbiome of a human, in particular a non-infant individual, to increase *Bifidobacterium* abundance and *Barnesiella* abundance. The method comprises administering, to said human, a composition comprising a mixture of 3'-SL, 3-FL and FSL, or a mixture of 3'-SL, LNT and LST-a, advantageously the first or second mixture of this invention, more advantageously the first mixture, as described above.

Another aspect of this invention relates to a method of preventing or treating viral and/or bacterial infections, especially antibiotic resistant bacterial infections, in a human, in particular a non-infant individual. The method comprises administering, to the human, a composition comprising a mixture of 3'-SL, 3-FL and FSL, or a mixture of 3'-SL, LNT and LST-a, advantageously the first or second mixture of this invention, more advantageously the first mixture, as described above.

DETAILED DESCRIPTION OF THE INVENTION

The present inventors has surprisingly discovered that a mixture of 3'-SL, 3-FL and FSL and a mixture of 3'-SL, LNT and LST-a possess anti-infective activity and therefore can be used as anti-infective compositions, e.g. for treating bacterial infections. The mixtures can increase *Bifidobacterium* abundance and *Barnesiella* abundance of the microbiome. The mixtures can also reduce Firmicutes abundance of the microbiome, especially *Clostridia* species. Humans having increased abundance of *Bifidobacterium* and *Barnesiella* in their microbiome are more resistant to a broad range of infections and recover more quickly from these infections. In particular, the present mixtures of HMOs are effective for protection against and recovery from antibiotic resistant infections. It is believed that this improved resistance and recovery is attributable to the health promoting changes in the microbiome caused by those HMOs. The capability to inhibit pathogen binding to the host body imparts additional health benefits.

1. HMO Mixtures

The present invention relates to synthetic HMO mixtures. The term "synthetic mixture" or "synthetic composition" designates a mixture or composition which is artificially prepared and preferably mean a mixture or composition containing at least one compound that is produced ex vivo chemically and/or biologically, e.g. by means of chemical reaction, enzymatic reaction or recombinantly. In this regard, "synthetic" is used as opposite to "natural", and means that a synthetic mixture or composition of the invention is not identical to a natural composition or mixture, like human milk, or at least one HMO of the mixture or the composition is not originated from a natural source, like e.g. human milk.

In one embodiment, the HMO mixture can be a first mixture of HMOs consisting essentially of three different HMOs, notably 3'-SL, an HMO component A which is 3-FL or LNT, and an HMO component B which is either FSL when component A is 3-FL, or LST-a when component A is LNT. In another embodiment, the HMO mixture of the invention is a second mixture which consists essentially of 3'-SL, a component A which is 3-FL or LNT, a component B which is either FSL when component A is 3-FL, or LST-a when component A is LNT, and lactose.

1.1. The First HMO Mixture

In one preferred embodiment, the first mixture of HMOs consists essentially of 3'-SL, 3-FL and FSL (first mixture I). The molar ratio of HMOs in the first mixture I may vary. In one embodiment, the molar ratio of FSL relative to a combination 3'-SL+3-FL is at least 1:20. In another embodiment, this ratio may be at least 1:12. Certain ratios of FSL relative to a combination 3'-SL+3-FL in the first mixture I, such as at least 1:5 or at least 1:3, may be preferred in some embodiments. In some other embodiments the first mixture I may have a molar ratio of 3'-SL relative to LNT of 0.05-5.3 or 0.17-3, preferably about 1.

In another preferred embodiment, the first mixture of HMOs consists essentially of 3'-SL, LNT and LST-a (first mixture II). The molar ratio of HMOs in first mixture II may vary. In one embodiment, the molar ratio of LST-a relative to a combination 3'-SL+LNT is at least 1:10. In another embodiment, this ratio may be at least 1:7. Certain rations of LST-a relative to a combination 3'-SL+LNT in first mixture II, such as at least 1:5 or around 1:3, may be preferred in some embodiments. The first mixture II may also have a molar ratio of 3'-SL relative to LNT of 0.05-11 or 0.13-7.7. In one preferred embodiment the molar ratio 3'-SL:LNT is about 1.

Any of the first HMO mixtures described above can be readily obtained by a process which involves treating a 3'-SL donor and a component A acceptor with an α2,3-transsialidase and then removing lactose and the α2,3-transsialidase from the reaction medium.

In one preferred embodiment, the process to make the first mixture I comprises a step of contacting 3'-SL and 3-FL in a molar ratio of preferably 1:3 to 3:1 or 1:2 to 2:1, such as around 1:1, with an α2,3-transsialidase having a conversion rate for the reaction of 3'-SL and 3-FL of at least 20%, up to about 90%, preferably at least 30% such as from at least 30% to about 80%, at least 40%, at least 50%, at least 60% or at least 70%. The reaction medium following the latter reaction, normally containing FSL, lactose, unreacted 3'-SL and 3-FL, and α2,3-transsialidase, is then subjected to conventional purification steps to remove substances other than 3'-SL, FSL and 3-FL, e.g. α2,3-transsialidase and lactose. If the later mixture is obtained by an in situ enzymatic reaction, the α2,3-transsialidase can be inactivated and removed, e.g. by denaturation followed by centrifugation or ultrafiltration, to produce a mixture consisting essentially of 3'-SL, 3-FL, FSL and lactose. The lactose in this mixture can then be separated from the 3'-SL, 3-FL and FSL, e.g. by cascade ultra- and/or nanofiltration, or the lactose can first be treated with lactase to degrade it to glucose and galactose which can then be separated from the 3'-SL, 3-FL and FSL by ultra- and/or nanofiltration. In case of producing the latter HMO mixture recombinantly, i.e. by a fermentation process using a genetically modified microorganism, such as a bacterium, expressing a recombinant α2,3-transsialidase, the purification of the HMO mixture may be done using steps of removal of the cell material from the fermentation broth followed by removing non-carbohydrate particulates and contaminants like salts, charged molecules, proteins, DNA, colorizing/caramel bodies, etc., to produce a mixture consisting essentially of 3'-SL, 3-FL, FSL and lactose. Separation of lactose can be conducted as described above.

In another preferred embodiment, the process to make the first mixture II comprises the step of contacting a mixture of 3'-SL and LNT, wherein the molar ratio of 3'-SL to LNT is in the range from 1:5 to 5:1, such as from 1:3 to 3:1, 1:2 to 2:1, or 1:1, with an α2,3-transsialidase having at least 30% to about 80% conversion rate for the reaction of 3'-SL and LNT, preferably at least 40%, such as at least 45%, at least 50%, at least 60% or more. The reaction medium following the latter reaction, normally containing LST-a, lactose, unreacted 3'-SL and LNT, and α2,3-transsialidase, is then subjected to conventional purification steps to remove substances other than 3'-SL, LNT and LST-a, e.g. α2,3-transsialidase and lactose. If the later mixture is obtained by an in situ enzymatic reaction, the α2,3-transsialidase can be inactivated and removed, e.g. by denaturation followed by centrifugation or ultrafiltration to produce a mixture consisting essentially of 3'-SL, LNT, LST-a and lactose. The lactose in this mixture can be separated from the 3'-SL, LNT and LST-a using well known procedures in the art, e.g. by a cascade ultra- and/or nanofiltration, or the lactose can first be treated with lactase to degrade it to glucose and galactose, which both can then be separated from the 3'-SL, LNT and LST-a by ultra- and/or nanofiltration. In case of producing the latter HMO mixture recombinantly, i.e. by a fermentation process using a genetically modified microorganism, such as a bacterium, expressing a recombinant α2,3-transsialidase, the purification of the HMO mixture may be done using steps of removal of the cell material from the fermentation broth followed by removing non-carbohydrate particulates and contaminants like salts, charged molecules, proteins, DNA, colorizing/caramel bodies, etc., to produce a mixture essentially consisting of 3'-SL, LNT, LST-a and lactose. Separation of lactose can be conducted as described above.

1.2. The Second HMO Mixture

The second HMO mixtures of the invention can be obtained by carrying out the process of this invention, as described above, which does not comprise a step of removing lactose from the obtained HMO mixtures.

In one embodiment, the second HMO mixture consists essentially of 3'-SL, 3-FL, FSL and lactose (second mixture I). Preferably, in this second mixture I:

the molar ratio of (3'-SL+3-FL) relative to FSL is 1-18, and the molar ratio of lactose relative to FSL is about 1.
More preferably, one of the molar ratios 3'-SL to FSL and 3-FL to FSL is not more than 3.

This second HMO mixture I can be obtained by carrying out the process of this invention with 3'-SL and 3-FL in a molar ratio of preferably 1:3 to 3:1, more preferably 1:2 to 2:1, even more preferably 1:1, and with an α2,3-transsialidase having a conversion rate of at least 20%, up to about 90%, preferably at least 35%, more preferably at least 50%. Preferably, in the second HMO mixture, the molar ratio of 3'-SL to 3-FL is 0.17-3.

In other embodiment, the second mixture of this invention consists essentially of 3'-SL, LNT, LST-a and lactose (second mixture II). Preferably, in this second mixture II:

the molar ratio of (3'-SL+LNT) relative to LST-a is 0.8-9.5, and the molar ratio of lactose relative to LST-a is about 1.
More preferably, one of the molar ratios 3'-SL to LST-a and LNT to LST-a is not more than 2.

This second HMO mixture II can be obtained by carrying out the process of this invention with 3'-SL and LNT in a molar ratio of preferably 1:5 to 5:1, more preferably 1:3 to 3:1, even more preferably 1:2 to 2:1, yet even more preferably 1:1, and with an α2,3-transsialidase having a conversion rate of at least 35%, up to about 80%, preferably at least 40%, more preferably at least 50%. Preferably, in the second HMO mixture II, the molar ratio of 3'-SL to LNT is 0.09-11.

1.3. Embodiments of the First and the Second HMO Mixtures

When the process of this invention is carried out with a molar ratio of 3'-SL to 3-FL of 2:1 to 1:2 and a conversion rate of 20-50%, a first or a second HMO mixture having a molar ratio of (3'-SL+3-FL) to FSL of 2-13 and a molar ratio of 3'-SL to 3-FL of 0.33-3 can be made.

When the process is carried out with a molar ratio of 3'-SL to 3-FL of 1:1 and a conversion rate of 20-50%, a first or a second HMO mixture having a molar ratio of (3'-SL+3-FL) to FSL of 2-8 and a molar ratio of 3'-SL to 3-FL of 1 can be made.

When the process is carried out with a molar ratio of 3'-SL to 3-FL of 3:1 to 1:3 and a conversion rate of 30-50%, a first or a second HMO mixture having a molar ratio of (3'-SL+3-FL) to FSL of 2-12 and a molar ratio of 3'-SL to 3-FL of 0.2-5 can be made.

When the process is carried out with a molar ratio of 3'-SL to 3-FL of 2:1 to 1:2 and a conversion rate of 30-50%, a first or a second HMO mixture having a molar ratio of (3'-SL+3-FL) to FSL of 2-8 and a molar ratio of 3'-SL to 3-FL of 0.33-3 can be made.

When the process is carried out with a molar ratio of 3'-SL to 3-FL of 1:1 and a conversion rate of 30-50%, a first or a second HMO mixture having a molar ratio of (3'-SL+3-FL) to FSL of 2-5 and a molar ratio of 3'-SL to 3-FL of 1 can be made.

When the process is carried out with a molar ratio of 3'-SL to 3-FL of 3:1 to 1:3 and a conversion rate of 30-60%, a first or a second HMO mixture having a molar ratio of (3'-SL+3-FL) to FSL of 2-12 and a molar ratio of 3'-SL to 3-FL of 0.17-6 can be made.

When the process is carried out with a molar ratio of 3'-SL to 3-FL of 2:1 to 1:2 and a conversion rate of 30-60%, a first or a second HMO mixture having a molar ratio of (3'-SL+3-FL) to FSL of 2-8 and a molar ratio of 3'-SL to 3-FL of 0.29-3.5 can be made.

When the process is carried out with a molar ratio of 3'-SL to 3-FL of 1:1 and a conversion rate of 30-60%, a first or a second HMO mixture having a molar ratio of (3'-SL+3-FL) to FSL of 2-4.67 and a molar ratio of 3'-SL to 3-FL of 1 can be made.

When the process is carried out with a molar ratio of 3'-SL to 3-FL of 3:1 to 1:3 and a conversion rate of 25-35%, a first or a second HMO mixture having a molar ratio of (3'-SL+3-FL) to FSL of 3.7-14 and a molar ratio of 3'-SL to 3-FL of 0.25-4.1 can be made.

When the process is carried out with a molar ratio of 3'-SL to 3-FL of 2:1 to 1:2 and a conversion rate of 25-35%, a first or a second HMO mixture having a molar ratio of (3'-SL+3-FL) to FSL of 3.7-10 and a molar ratio of 3'-SL to 3-FL of 0.39-2.54 can be made.

When the process is carried out with a molar ratio of 3'-SL to 3-FL of 1:1 and a conversion rate of 25-35%, a first or a second HMO mixture having a molar ratio of (3'-SL+3-FL) to FSL of 3.7-6 and a molar ratio of 3'-SL to 3-FL of 1 can be made.

When the process is carried out with a molar ratio of 3'-SL to 3-FL of 3:1 to 2:1 and a conversion rate of 30-60%, a first or a second HMO mixture having a molar ratio of (3'-SL+3-FL) to FSL of 3-12 and a molar ratio of 3'-SL to 3-FL of 2.43-6 can be made.

When the process is carried out with a molar ratio of 3'-SL to 3-FL of 2:1 to 1:1 and a conversion rate of 20-50%, a first or a second HMO mixture having a molar ratio of (3'-SL+3-FL) to FSL of 2-13 and a molar ratio of 3'-SL to 3-FL of 1-3 can be made.

When the process is carried out with a molar ratio of 3'-SL to 3-FL of 1:1 to 1:2 and a conversion rate of 30-60%, a first or a second HMO mixture having a molar ratio of (3'-SL+3-FL) to FSL of 2-8 and a molar ratio of 3'-SL to 3-FL of 0.29-1 can be made.

When the process is carried out with a molar ratio of 3'-SL to 3-FL of 1:2 to 1:3 and a conversion rate of 40-90%, a first or a second HMO mixture having a molar ratio of (3'-SL+3-FL) to FSL of 1.75-8 and a molar ratio of 3'-SL to 3-FL of 0.05-0.38 can be made.

When the process is carried out with a molar ratio of 3'-SL to 3-FL of 2:1 to 1:3 and a conversion rate of 20-50%, a first or a second HMO mixture having a molar ratio of (3'-SL+3-FL) to FSL of 2-18 and a molar ratio of 3'-SL to 3-FL of less than 3.5 can be made.

When the process of this invention is carried out with a molar ratio of 3'-SL to LNT of 2:1 to 1:2 and a conversion rate of 35-70%, a first or a second HMO mixture having a molar ratio of (3'-SL+LNT) to LST-a of 0.8-6.6 and a molar ratio of 3'-SL to LNT of 0.2-4.5 can be made.

When the process is carried out with a molar ratio of 3'-SL to LNT of 1:1 and a conversion rate of 35-70%, a first or a second HMO mixture having a molar ratio of (3'-SL+LNT) to LST-a of 0.8-3.8 and a molar ratio of 3'-SL to LNT of 1 can be made.

When the process is carried out with a molar ratio of 3'-SL to LNT of 3:1 to 1:3 and a conversion rate of 40-80%, a first or a second HMO mixture having a molar ratio of (3'-SL+LNT) to LST-a of 0.5-8 and a molar ratio of 3'-SL to LNT of 0.09-11 can be made.

When the process is carried out with a molar ratio of 3'-SL to LNT of 2:1 to 1:2 and a conversion rate of 40-70%, a first or a second HMO mixture having a molar ratio of (3'-SL+LNT) to LST-a of 0.8-5.5 and a molar ratio of 3'-SL to LNT of 0.2-4.5 can be made.

When the process is carried out with a molar ratio of 3'-SL to LNT of 1:1 and a conversion rate of 40-70%, a first or a second HMO mixture having a molar ratio of (3'-SL+LNT) to LST-a of 0.8-3 and a molar ratio of 3'-SL to LNT of 1 can be made.

When the process is carried out with a molar ratio of 3'-SL to LNT of 3:1 to 1:3 and a conversion rate of 50-80%, a first or a second HMO mixture having a molar ratio of (3'-SL+LNT) to LST-a of 0.5-6 and a molar ratio of 3'-SL to LNT of 0.09-11 can be made.

When the process is carried out with a molar ratio of 3'-SL to LNT of 2:1 to 1:2 and a conversion rate of 50-70%, a first or a second HMO mixture having a molar ratio of (3'-SL+LNT) to LST-a of 0.8-4 and a molar ratio of 3'-SL to LNT of 0.2-4.5 can be made.

When the process is carried out with a molar ratio of 3'-SL to LNT of 1:1 and a conversion rate of 50-70%, a first or a second HMO mixture having a molar ratio of (3'-SL+LNT) to LST-a of 0.8-2 and a molar ratio of 3'-SL to LNT of 1 can be made.

When the process is carried out with a molar ratio of 3'-SL to LNT of 3:1 to 1:3 and a conversion rate of 40-60%, a first or a second HMO mixture having a molar ratio of (3'-SL+LNT) to LST-a of 1.3-8 and a molar ratio of 3'-SL to LNT of 0.17-6 can be made.

When the process is carried out with a molar ratio of 3'-SL to LNT of 2:1 to 1:2 and a conversion rate of 40-60%, a first or a second HMO mixture having a molar ratio of (3'-SL+LNT) to LST-a of 2-6.6 and a molar ratio of 3'-SL to LNT of 0.25-3.5 can be made.

When the process is carried out with a molar ratio of 3'-SL to LNT of 1:1 and a conversion rate of 40-60%, a first or a second HMO mixture having a molar ratio of (3'-SL+LNT) to LST-a of 1.3-3 and a molar ratio of 3'-SL to LNT of 1 can be made.

When the process is carried out with a molar ratio of 3'-SL to LNT of 5:1 to 3:1 and a conversion rate of 50-80%, a first or a second HMO mixture having a molar ratio of (3'-SL+LNT) to LST-a of 3-10 and a molar ratio of 3'-SL to LNT of 5-21 can be made.

When the process is carried out with a molar ratio of 3'-SL to LNT of 3:1 to 2:1 and a conversion rate of 40-80%, a first or a second HMO mixture having a molar ratio of (3'-SL+LNT) to LST-a of 1.75-8 and a molar ratio of 3'-SL to LNT of 2.5-11 can be made.

When the process is carried out with a molar ratio of 3'-SL to LNT of 2:1 to 1:1 and a conversion rate of 35-70%, a first or a second HMO mixture having a molar ratio of (3'-SL+LNT) to LST-a of 0.86-6.6 and a molar ratio of 3'-SL to LNT of 1-4.3 can be made.

When the process is carried out with a molar ratio of 3'-SL to LNT of 1:1 to 1:2 and a conversion rate of 35-70%, a first or a second HMO mixture having a molar ratio of (3'-SL+LNT) to LST-a of 0.86-6.6 and a molar ratio of 3'-SL to LNT of 0.23-1 can be made.

When the process is carried out with a molar ratio of 3'-SL to LNT of 1:2 to 1:3 and a conversion rate of 40-80%, a first or a second HMO mixture having a molar ratio of (3'-SL+LNT) to LST-a of 1.75-8 and a molar ratio of 3'-SL to LNT of 0.09-0.4 can be made.

When the process is carried out with a molar ratio of 3'-SL to LNT of 1:3 to 1:5 and a conversion rate of 50-80%, a first or a second HMO mixture having a molar ratio of (3'-SL+LNT) to LST-a of 3-10 and a molar ratio of 3'-SL to LNT of 0.05-0.2 can be made.

1.4. Enzymatic Production of HMO Mixtures of the Invention

In accordance with this invention, the term "α2,3-trans-sialidase" means any wild type or engineered sialidase that is able to transfer a sialyl residue to the 3-position of the glucose in an acceptor of formula 2, to the 3-position of the N-acetyl-glucosamine in a, preferably terminal, N-acetyl-lactosaminyl group in an acceptor of formula 1, 1a or 1b, or to the 4-position of the N-acetyl-glucosamine in a, preferably terminal, lacto-N-biosyl group, in an acceptor of formula 1, 1a or 1b, where the compounds of formulae 1 and 2 are as follows:

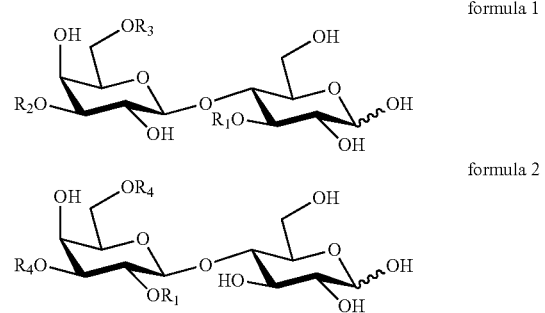

wherein $R_1$ is fucosyl or H, $R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, $R_3$ is H or N-acetyl-lactosaminyl group optionally substituted with a glycosyl residue comprising one or more N-acetyl-lactosaminyl and/or one or more lacto-N- biosyl groups; any N-acetyl-lactosaminyl and lacto-N-biosyl group can be substituted with one or more sialyl and/or fucosyl residue, and each $R_4$ independently is sialyl or H, with the proviso that at least one of $R_1$ or $R_4$ is not H; and the compounds of formulae 1a and 1b are as follows:

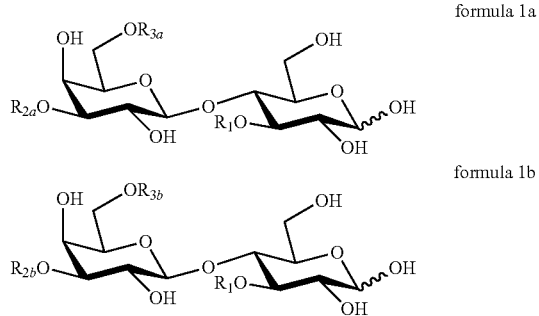

wherein $R_1$ is as defined above, $R_{2a}$ is an N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue, but preferably void of a sialyl and/or fucosyl residue, $R_{3a}$ is H or an N-acetyl-lactosaminyl group optionally substituted with a lacto-N-biosyl group; any N-acetyl-lactosaminyl and lacto-N-biosyl group can be substituted with one or more sialyl and/or fucosyl residue, but preferably void of a sialyl and/or fucosyl residue, $R_{2b}$ is a lacto-N-biosyl group optionally substituted with sialyl and/or fucosyl residue, but preferably void of a sialyl and/or fucosyl residue, and $R_{3b}$ is H or an N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue, but preferably without a sialyl and/or fucosyl residue.

Preferably, the compounds of formulae 1a and 1 b have one or more of the following linkages and modifications:

the N-acetyl-lactosaminyl group in the glycosyl residue of $R_{2a}$ in formula 1a is attached to the another N-acetyl-lactosaminyl group by a 1-3 interglycosidic linkage, the lacto-N-biosyl group in the glycosyl residue of $R_{2a}$ in formula 1a is attached to the N-acetyl-lactosaminyl group by a 1-3 interglycosidic linkage, the lacto-N-biosyl group in the glycosyl residue of $R_{3a}$ in formula 1a is attached to the N-acetyl-lactosaminyl group by a 1-3 interglycosidic linkage, the N-acetyl-lactosaminyl group in the glycosyl residue of $R_{3b}$ in formula 1 b is attached to another N-acetyl-lactosaminyl group by a 1-3 or 1-6 interglycosidic linkage, and the lacto-N-biosyl group in the glycosyl residue of $R_{3b}$ in formula 1 b is attached to the N-acetyl-lactosaminyl group by a 1-3 interglycosidic linkage.

The α2,3-transsialidase used in the processes of this invention is preferably the α2,3-transsialidase (TcTS) from *Trypanosoma cruzi*. However, the α2,3-transsialidases from other microorganisms, such as *T. rangeli*, *T. brucei gambiense*, *T. brucei rhodesiense*, *T. brucei brucei*, *T. congolense* and *Corynebacterium diphtheriae* as described in WO 2012/156898, as well as the α2,3-transsialidases from *Salmonella typhimurium*, *Bacteroides fragilis*, Newcastle disease virus and *Vibrio cholera*, can be used. Moreover, other α2,3-transsialidases can also be used which have at least 60%, preferably at least 70%, more preferably at least 80%, particularly at least 90%, identity with the α2,3-transsialidase from *T. cruzi*.

Preferably, the transsialidase activity of the α2,3-transsialidase is greater than its hydrolytic activity. In the course of the 3'-SL+3-FL ⇌ FSL+Lac or 3'-SL+LNT ⇌ LST-a+Lac reaction the hydrolysis of FSL or LST-a can become significant at a certain time point, due to the increasing concentration of FSL or LST-a, which is then degraded into 3-FL or LNT, respectively, and sialic acid. In order to prepare the HMO mixtures of the invention, the reaction should be stopped before there is significant product hydrolysis. This time point can be easily determined by well-known enzyme kinetic measurements.

The α2,3-transsialidases for making the HMO mixtures of this invention are preferably selected from the α2,3-transsialidases that lack hydrolytic activity, or at least have significantly reduced hydrolytic activity. Such enzymes can be made by altering the amino acid sequence of a mainly wild type, α2,3-transsialidase at one or more amino acid positions, so that the mutated amino acid sequence results in improved transsialidase activity and/or reduced hydrolytic activity.

In carrying out the process of this invention, particular relative concentrations of the 3'-SL donor, 3-FL or LNT acceptor, the α2,3-transsialidase, the aqueous solvent and the incubation buffer (e.g. 50 mM $Na_3PO_4$ or 100 mM $KHPO_4$) are not critical. In this regard, the process can be suitably carried out at room temperature (e.g. 15-50, preferably 20-37° C.) at a pH of 6-8, preferably 6.5-7 for 15 min to 24 hours.

In one preferred embodiment, any of the HMO mixtures of the invention are produced by a genetically modified microorganism to express an α2,3-transsialidase as described above. Methods of genetic modifications of microorganisms for recombinant production of biologically active molecules and molecular manipulation of enzyme molecules are well-known in the art, see e.g. Green M R & Sambrook J: Molecular Cloning: A Laboratory Manual, 4th ed, 2012, CSHL PRESS.

2. Use of the HMO Mixtures of the Invention

Surprisingly, the HMO mixtures containing 3'-SL, a component A which is 3-FL or LNT, and a component B which is FSL when component A is 3-FL or LST-a when component A is LNT, as any one of the described herein, are anti-infective compositions and therefore they can be advantageously used for treating viral and/or bacterial infections. Preferably, the anti-infective composition comprises a mixture of HMOs consisting essentially of 3'-SL, a component A which is 3-FL or LNT, and a component B which is FSL when component A is 3-FL or LST-a when component A is LNT. Also preferably, the anti-infective composition comprises a mixture of HMOs consisting essentially of 3'-SL, a component A which is 3-FL or LNT, a component B which is FSL when component A is 3-FL or LST-a when component A is LNT, and lactose.

Accordingly, in one embodiment, the anti-infective compositions of this invention can be pharmaceutical compositions. The pharmaceutical compositions may further contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical compositions of the invention may also contain other materials that do not produce an adverse, allergic or otherwise unwanted reaction when administered to a patient. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or nonaqueous techniques.

In other embodiment, the anti-infective compositions of this invention can be nutritional compositions. For example, a nutritional composition of the invention may be formulated as a rehydration solution, or a dietary maintenance or supplement for elderly individuals or immunocompromised individuals. Macronutrients such as edible fats, carbohydrates and proteins can also be included in such nutritional compositions. Edible fats include, for example, coconut oil, soy oil and monoglycerides and diglycerides. Carbohydrates include, for example, glucose, edible lactose and hydrolysed cornstarch. Proteins include, for example, soy protein, whey, and skim milk. Vitamins and minerals (e. g. calcium, phosphorus, potassium, sodium, chloride, magnesium, manganese, iron, copper, zinc, selenium, iodine, and Vitamins A, E, D, C, and B complex) can also be included in such nutritional compositions.

The anti-infective compositions of this invention can be administered orally, e.g. as a tablet, capsule, or pellet containing a predetermined amount of the first or second mixture, or as a powder or granules containing a predetermined concentration of the first or second mixture, or a gel, paste, solution, suspension, emulsion, syrup, bolus, electuary, or slurry, in an aqueous or nonaqueous liquid, containing a predetermined concentration of the first or second mixture. Orally administered compositions can include binders, lubricants, inert diluents, flavouring agents, and humectants. Orally administered compositions such as tablets can optionally be coated and can be formulated so as to provide sustained, delayed or controlled release of the first or second mixture therein.

The anti-infective compositions of this invention, advantageously a pharmaceutical composition, can also be administered by rectal suppository, aerosol tube, naso-gastric tube or direct infusion into the GI tract or stomach.

Anti-infective pharmaceutical compositions of this invention can additionally comprise other therapeutic agents such as antiviral agents, antibiotics, probiotics, analgesics, and anti-inflammatory agents.

The proper dosage of the anti-infective compositions for a patient can be determined in a conventional manner, based upon factors such as the patient's immune status, body weight and age. In some cases, the dosage will be at a concentration similar to that found for 3'-SL, 3-FL and/or FSL, or 3'-SL, LNT and/or LST-a, in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by methods known to those skilled in the art.

In another aspect, the invention provides a method of modulating the microbiome of a human, particularly of a non-infant, to increase *Bifidobacterium* abundance and *Barnesiella* abundance, the method comprising administering, to the human, a mixture comprising 3'-SL, a component A which is 3-FL or LNT, and a component B which is FSL when component A is 3-FL or LST-a when component A is LNT, preferably a mixture consisting essentially of 3'-SL, a component A which is 3-FL or LNT, and a component B which is FSL when component A is 3-FL or LST-a when component A is LNT, or a mixture consisting essentially of 3'-SL, a component A which is 3-FL or LNT, a component B which is FSL when component A is 3-FL or LST-a when component A is LNT, and lactose.

"Non-infant human", "non-infant individual" or "non-infant" preferably means a human of 3 years of age and older. A non-infant human can be a child, a teenager, an adult or an elderly.

In still another aspect, the invention provides a method of preventing or treating viral and/or bacterial infections, especially antibiotic resistant bacterial infections, in a human, particularly in a non-infant, the method comprising administering, to the human, a mixture comprising 3'-SL, a component A which is 3-FL or LNT, and a component B which is FSL when component A is 3-FL or LST-a when component A is LNT, preferably a mixture consisting essentially of 3'-SL, a component A which is 3-FL or LNT, and a component B which is FSL when component A is 3-FL or LST-a when component A is LNT, or a mixture consisting essentially of 3'-SL, a component A which is 3-FL or LNT, a component B which is FSL when component A is 3-FL or LST-a when component A is LNT, and lactose.

Whilst the invention has been described with reference to a preferred embodiment, it will be appreciated that various modifications are possible within the scope of the invention.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

EXAMPLES

In the examples below, the α2,3-transsialidase from *T. cruzi* (TcTS) was used for making mixtures of this invention.

Example 1

3'-SL+3-FL ⇌ FSL+Lac

The test was run in Gibco PBS 1-X buffer (pH=7.5, 25° C., 200 µl), enzyme extract=0.05 mg/ml. HPLC conditions: TSK Gel amide 80 (Tosoh, 3 µm, 150×4.6 mm) was used with a flow of 1.1 ml/min using 70% acetonitrile and 30% ammonium formate (8 mM). The elution of substrates and products was detected by CAD and/or UV detection at 195 nm.

The tables below show the composition of mixtures obtained. Lactose is equimolar to FSL.

| 3'-SL/3-FL ratio: 3/4 | | | | |
| --- | --- | --- | --- | --- |
| time (h) | FSL conversion | 3'-SL (mol %) | 3-FL (mol %) | FSL (mol %) |
| 1.5 | 12% | 38% | 52% | 5% |
| 2.5 | 18% | 35% | 49% | 8% |

-continued

| 3'-SL/3-FL ratio: 3/4 | | | | |
|---|---|---|---|---|
| time (h) | FSL conversion | 3'-SL (mol %) | 3-FL (mol %) | FSL (mol %) |
| 5 | 25% | 32% | 46% | 11% |
| 21 | 36% | 27% | 42% | 15% |

| 3'-SL/3-FL ratio: 1/2 | | | | |
|---|---|---|---|---|
| time (h) | FSL conversion | 3'-SL (mol %) | 3-FL (mol %) | FSL (mol %) |
| 21 | 23% | 26% | 59% | 8% |

Example 2

3'-SL + 3-FL ⇌ FSL + Lac

The test was run in Gibco PBS 1-X buffer (pH=7.5, 25° C., 200 μl), enzyme extract=1 mg/ml. HPLC conditions: TSK Gel amide 80 (Tosoh, 3 μm, 150×4.6 mm) was used with a flow of 1.1 ml/min using 70% acetonitrile and 30% ammonium formate (8 mM). The elution of substrates and products was detected by CAD and/or UV detection at 195 nm.

The tables below show the composition of mixtures obtained. Lactose is equimolar to FSL.

| 3'-SL/3-FL ratio: 1/1 | | | | |
|---|---|---|---|---|
| time (h) | FSL conversion | 3'-SL (mol %) | 3-FL (mol %) | FSL (mol %) |
| 0.25 | 9% | 46% | 45% | 5% |
| 0.50 | 13% | 44% | 44% | 6% |
| 0.75 | 16% | 48% | 39% | 7% |
| 1.00 | 17% | 42% | 41% | 9% |
| 1.67 | 23% | 39% | 39% | 12% |
| 2.67 | 28% | 36% | 38% | 15% |
| 4.5 | 34% | 32% | 35% | 18% |
| 6 | 39% | 31% | 33% | 21% |
| 9 | 40% | 28% | 31% | 21% |

| 3'-SL/3-FL ratio: 2/1 | | | | |
|---|---|---|---|---|
| time (h) | FSL conversion | 3'-SL (mol %) | 3-FL (mol %) | FSL (mol %) |
| 0.25 | 10% | 60% | 31% | 4% |
| 0.50 | 16% | 59% | 29% | 5% |
| 0.75 | 21% | 57% | 28% | 7% |
| 1.00 | 22% | 57% | 28% | 8% |
| 1.67 | 28% | 53% | 26% | 10% |
| 2.67 | 35% | 50% | 24% | 13% |
| 4.5 | 41% | 48% | 22% | 15% |
| 6 | 47% | 46% | 21% | 18% |
| 9 | 51% | 39% | 20% | 21% |

| 3'-SL/3-FL ratio: 3/1 | | | | |
|---|---|---|---|---|
| time (h) | FSL conversion | 3'-SL (mol %) | 3-FL (mol %) | FSL (mol %) |
| 0.25 | 11% | 68% | 24% | 3% |
| 0.50 | 18% | 67% | 22% | 5% |
| 0.75 | 22% | 65% | 22% | 6% |
| 1.00 | 24% | 67% | 21% | 7% |
| 1.67 | 32% | 61% | 20% | 9% |
| 2.67 | 39% | 59% | 18% | 12% |
| 4.5 | 45% | 56% | 16% | 13% |
| 6 | 51% | 54% | 15% | 16% |
| 9 | 53% | 47% | 16% | 17% |

| 3'-SL/3-FL ratio: 1/2 | | | | |
|---|---|---|---|---|
| time (h) | FSL conversion | 3'-SL (mol %) | 3-FL (mol %) | FSL (mol %) |
| 0.25 | 17% | 30% | 59% | 6% |
| 0.50 | 24% | 27% | 57% | 9% |
| 0.75 | 27% | 26% | 56% | 9% |
| 1.00 | 32% | 25% | 55% | 11% |
| 1.67 | 41% | 21% | 52% | 14% |
| 2.67 | 48% | 18% | 49% | 17% |
| 4.5 | 59% | 14% | 49% | 19% |
| 6 | 64% | 13% | 46% | 23% |
| 9 | 73% | 9% | 40% | 24% |

| 3'-SL/3-FL ratio: 1/3 | | | | |
|---|---|---|---|---|
| time (h) | FSL conversion | 3'-SL (mol %) | 3-FL (mol %) | FSL (mol %) |
| 0.25 | 25% | 20% | 67% | 7% |
| 0.50 | 33% | 18% | 67% | 9% |
| 0.75 | 41% | 16% | 63% | 11% |
| 1.00 | 45% | 15% | 63% | 12% |
| 1.67 | 58% | 11% | 61% | 15% |
| 2.67 | 68% | 8% | 58% | 17% |
| 4.5 | 78% | 6% | 55% | 20% |
| 6 | 80% | 6% | 54% | 22% |
| 9 | 84% | 4% | 54% | 20% |

Example 3

3'-SL + LNT ⇌ LST-a + Lac

The test was run in Gibco PBS 1-X buffer (pH=7.5, 25° C., 200 μl), enzyme extract=0.05 mg/ml. HPLC conditions: TSK Gel amide 80 (Tosoh, 3 μm, 150×4.6 mm) was used with a flow of 1.1 ml/min using 70% acetonitrile and 30% ammonium formate. The elution of substrates and products was detected by CAD and/or UV detection at 195 nm.

The tables below show the composition of mixtures obtained. Lactose is equimolar to LST-a.

| 3'-SL/LNT ratio: 1/1 | | | | |
|---|---|---|---|---|
| time (h) | LST-a conversion | 3'-SL (mol %) | LNT (mol %) | LST-a (mol %) |
| 0 | 0 | 51% | 49% | 0% |
| 0.25 | 13% | 44% | 44% | 6% |
| 0.5 | 16% | 41% | 41% | 8% |
| 2 | 38% | 30% | 31% | 19% |
| 3 | 43% | 29% | 28% | 21% |
| 4 | 46% | 28% | 25% | 22% |
| 5 | 47% | 27% | 26% | 23% |
| 6 | 49% | 26% | 23% | 22% |

3'-SL/LNT ratio: 2/1

| time (h) | LST-a conversion | 3'-SL (mol %) | LNT (mol %) | LST-a (mol %) |
|---|---|---|---|---|
| 0 | 0 | 68% | 32% | 0% |
| 0.25 | 21% | 59% | 26% | 7% |
| 0.5 | 27% | 58% | 24% | 9% |
| 2 | 53% | 51% | 15% | 16% |
| 3 | 58% | 48% | 13% | 19% |
| 4 | 65% | 47% | 11% | 20% |
| 5 | 67% | 46% | 11% | 22% |
| 6 | 66% | 48% | 9% | 17% |
| 7 | 64% | 47% | 10% | 18% |

3'-SL/LNT ratio: 3/1

| time (h) | LST-a conversion | 3'-SL (mol %) | LNT (mol %) | LST-a (mol %) |
|---|---|---|---|---|
| 0 | 0 | 73% | 27% | 0% |
| 0.25 | 23% | 66% | 20% | 6% |
| 0.5 | 34% | 63% | 17% | 9% |
| 2 | 60% | 58% | 10% | 15% |
| 3 | 66% | 56% | 9% | 17% |
| 4 | 70% | 56% | 7% | 16% |
| 5 | 66% | 54% | 8% | 15% |
| 6 | 77% | 56% | 5% | 17% |
| 24 | 73% | 53% | 7% | 19% |

3'-SL/LNT ratio: 1/2

| time (h) | LST-a conversion | 3'-SL (mol %) | LNT (mol %) | LST-a (mol %) |
|---|---|---|---|---|
| 0 | 0% | 31% | 69% | 0% |
| 0.25 | 23% | 24% | 61% | 7% |
| 0.5 | 33% | 20% | 59% | 10% |
| 2 | 62% | 11% | 49% | 19% |
| 3 | 67% | 10% | 48% | 21% |
| 4 | 68% | 10% | 47% | 22% |
| 5 | 66% | 10% | 47% | 20% |
| 6 | 63% | 10% | 46% | 16% |
| 7 | 64% | 11% | 44% | 19% |

3'-SL/LNT ratio: 1/3

| time (h) | LST-a conversion | 3'-SL (mol %) | LNT (mol %) | LST-a (mol %) |
|---|---|---|---|---|
| 0 | 0% | 41% | 59% | 0% |
| 0.25 | 24% | 22% | 61% | 7% |
| 0.5 | 40% | 18% | 56% | 12% |
| 2 | 72% | 9% | 45% | 22% |
| 3 | 73% | 7% | 53% | 19% |
| 4 | 71% | 7% | 56% | 17% |
| 5 | 71% | 5% | 63% | 13% |
| 6 | 73% | 7% | 46% | 19% |
| 7 | 70% | 9% | 46% | 20% |

Example 4

A total of 30 male and female patients are recruited to participate in the study. After a screening visit and run-in period of 1-2 weeks, the patients are selected and randomized into three groups, each of 10 patients. Two groups are administered a treatment product containing 5 grams of a combination of 3-FL, 3'-SL and FSL, and 3'-SL, LNT and LST-a, respectively, and one group the placebo product (2 grams of glucose) for 8 weeks. The products and the placebo are in powder form in a unit dosage container.

The patients are eligible to participate if they are at least 18 years of age. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep their samples in the freezer until the next visit.

At the second visit, eligibility criteria are checked and eligible subjects are randomised to the three arms in the trial. The faecal samples are collected and equipment for new samples are distributed. Patients are familiarised with an interactive internet enabled system which records data daily and are provided with either treatment or control products. Subjects are reminded not to change their usual diet during the study. Blood samples are collected for biomarker studies. The faecal samples are stored at −80° C. until analysis. Faecal samples are subjected to 16 S RNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:
Bristol Stool Form Scale (BSF) information,
symptom information such as abdominal pain, abdominal discomfort, abdominal cramping, abdominal bloating, and abdominal fullness,
additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each patient has an exit visit with the medical team. Faecal samples and blood samples are collected and analysed as before.

The faecal analysis indicates that the treatment patients have increased abundance of *Bifidobacterium* and *Barnesiella*.

Example 5

Thirty 7-week-old C57BL/6J female mice are individually housed to avoid contamination between mice and provided with irradiated food and water. The mice are separated into 3 groups of 10 mice, 2 treatment groups and a placebo group.

The mice are treated with ampicillin (0.5 g/liter) in their drinking water, which is changed every 3 days. After 1 week, the ampicillin addition to the drinking water is terminated. Thereafter 3-FL, 3'-SL and FSL, and 3'-SL, LNT and LST-a, are added to the drinking water of the treatment groups, respectively, at a total concentration of 40 mg/ml. The control group receives plain water. Fresh water is administered daily and all mice have free access to the drinking water. The mice are fed a rodent chow and are given fresh chow daily.

Two days after termination of the ampicillin treatment, mice of each group are infected by means of oral gavage with a vancomycin-resistant *Enterococcus faecium* strain (VRE). VRE levels are determined at different time points by plating serial dilutions of faecal pellets on Enterococcosel agar plates with vancomycin. VRE colonies are identified by appearance and confirmed by Gram staining. PCR of the vanA gene, which confers resistance to vancomycin, is used to confirm the presence of VRE in infected mice.

The mice are monitored for 2 weeks and are then euthanized. Fresh stool pellets are obtained before the mice are euthanized. The samples are immediately frozen and stored at −80° C. DNA is extracted using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res*. 41, e1 (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries wisas measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

In the HMO treated mice, VRE colonisation is reduced to undetectable levels within 14 days. The density of VRE reduces within 5 days. The untreated mice continue to harbour large numbers of VRE in the colon. The treatment groups of mice also show an increased abundance of Porphyromonadaceae, especially *Barnesiella*.

The invention claimed is:

1. A mixture of human milk oligosaccharides consisting essentially of:
   (a) 3'-O-sialyllactose, and
   (b) 3-O-fucosyllactose and 3-O-fucosyl-3'-O-sialyllactose; or
   lacto-N-tetraose and sialyllacto-N-tetraose a, which is obtained by a process comprising the steps of reacting 3'-O-sialyllactose and 3-O-fucosyllactose or lacto-N-tetraose in the presence of an α2,3-transsialidase to produce a reaction medium, removing the α2,3-transsialidase from the reaction medium, and optionally removing lactose,
wherein the step of reacting 3'-O-sialyllactose and 3-O-fucosyllactose in a molar ratio of 1:2 to 1:3, in the presence of an α2,3-transsialidase having a conversion rate of 40-90%, for the reaction of 3'-O-sialyllactose and 3-O-fucosyllactose; or
wherein the step of reacting 3'-O-sialyllactose and lacto-N-tetraose in a molar ratio of 3:1 to 1:3, in the presence of an α2,3-transsialidase having a conversion rate of at least 35%, up to about 80%, for the reaction of 3'-O-sialyllactose and lacto-N-tetraose.

2. A process for obtaining the mixture of human milk oligosaccharides consisting essentially of:
   (a) 3'-O-sialyllactose, and
   (b) 3-O-fucosyllactose and 3-O-fucosyl-3'-O-sialyllactose; or
   lacto-N-tetraose and sialyllacto-N-tetraose a, comprising the steps of reacting 3'-O-sialyllactose and 3-O-fucosyllactose or lacto-N-tetraose in the presence of an α2,3-transsialidase to produce a reaction medium, and then removing the α2,3-transsialidase from the reaction medium,
wherein the step of reacting 3'-O-sialyllactose and 3-O-fucosyllactose in a molar ratio of 1:2 to 1:3, in the presence of an α2,3-transsialidase having a conversion rate of 40-90%, for the reaction of 3'-O-sialyllactose and 3-O-fucosyllactose; or
wherein the step of reacting 3'-O-sialyllactose and lacto-N-tetraose in a molar ratio of 3:1 to 1:3, in the presence of an α2,3-transsialidase having a conversion rate of at least 35%, up to about 80%, for the reaction of 3'-O-sialyllactose and lacto-N-tetraose.

3. An anti-infective composition for treating bacterial infections comprising the mixture of claim 1.

4. A method of modulating the microbiome of a human to increase *Bifidobacterium* abundance and *Barnesiella* abundance, the method comprising administering, to the human, the mixture of claim 1.

5. A method of preventing or treating viral and/or bacterial infections in a human, the method comprising administering, to the human, a mixture comprising the mixture of claim 1.

* * * * *